United States Patent [19]

Buturovic-Ponikvar

[11] Patent Number: 5,709,993
[45] Date of Patent: Jan. 20, 1998

[54] PROCESS FOR ANTICOAGULATION DURING EXTRACORPOREAL BLOOD CIRCULATION SEQUENTIALLY USING CITRATE OR NAFAMOSTAT AND HEPARIN

[76] Inventor: Jadranka Buturovic-Ponikvar, Rusjanov trg 8, 1000 Ljubljana, Slovenia

[21] Appl. No.: 605,005

[22] PCT Filed: Jul. 13, 1995

[86] PCT No.: PCT/SI95/00016

§ 371 Date: May 20, 1996

§ 102(e) Date: May 20, 1996

[87] PCT Pub. No.: WO96/02288

PCT Pub. Date: Feb. 1, 1996

[30] Foreign Application Priority Data

Jul. 13, 1994 [SI] Slovenia ................ P-9400289

[51] Int. Cl.⁶ .................................................. A61M 1/14
[52] U.S. Cl. ........................ 435/2; 514/56; 514/574; 514/822; 210/646; 210/645
[58] Field of Search ................ 435/2; 514/574, 514/822, 56; 210/645, 646

[56] References Cited

U.S. PATENT DOCUMENTS 5,032,615  7/1991  Ward et al. .................. 514/574
5,407,581  4/1995  Onodera et al. ............... 210/654

OTHER PUBLICATIONS

Wallmark A. et al., Artificial Organs 8(1): 72–81 (1984).
Akizawa T. et al., Nephron 64(3): 376–81 (1993).

*Primary Examiner*—Sandra E. Saucier
*Attorney, Agent, or Firm*—Pollock, Vande, Sande & Priddy

[57] ABSTRACT

Process for preventing activation of enzyme systems such as coagulation and activation of complement system or bradykinin system in extracorporeal blood circulation in haemodialysis and similar procedures, by means of sequential anticoagulation, which comprises adding in the first 15 to 30 minutes of haemodialysis or of similar procedure, sodium citrate or nafamostat mesylate, into a dialysis line as anticoagulant, then stopping the addition of citrate or nafomostat mesylate, and adding heparin in the conventional total dose, until the end of dialysis.

By using this process, a universal routine haemodialysis or a similar procedure, is made possible without further adaptations according to the kind of patient.

8 Claims, 1 Drawing Sheet

PROCESS FOR ANTICOAGULATION DURING EXTRACORPOREAL BLOOD CIRCULATION SEQUENTIALLY USING CITRATE OR NAFAMOSTAT AND HEPARIN

TECHNICAL FIELD

The present invention is from the field of medicine and relates to a process for preventing activation of enzyme systems in haemodialysis and in similar procedures with extracorporeal blood circulation by means of sequential anticoagulation.

TECHNICAL PROBLEM

There was a need for a simple and effective way of preventing the activation of enzyme systems in extracorporeal blood circulation in haemodialysis and in similar procedures.

PRIOR ART

Haemodialysis partly replaces the kidney function in patients with renal failure. A scheme of haemodialysis is shown in FIG. 1. The blood stream 7 of the patient flows along the arterial blood line by means of a blood pump 1. An anticoagulant 2 is added to the line, then blood passes into an arterial bubble trap 3 (preventing the invasion of air into the dialyser 4) and into a dialyser 4. From the dialyser 4 blood passes through a venous bubble trap 6 (preventing the entry of air into the patient) along the venous blood line into the patient's body. From the other side of the membrane of the dialyser 4 the flow of dialyse solution 5 flows into the dialyser 4. Solutes and water pass the semipermeable membrane of the dialyser 4 from the plasma into the dialyse solution 5 and vice versa.

At the contact of blood with artificial surfaces such as dialyser membranes or surfaces of blood tubing, different enzyme systems in blood are activated. Most important is the activation of thrombocytes and of the coagulation system, which leads to total blood coagulation in the extracorporeal blood circulation. For the prevention thereof anticoagulants and anticoagulating processes must be applied during haemodialysis or procedures similar thereto. A standard routine anticoagulation during haemodialysis or similar procedures with extracorporeal blood circulation is anticoagulation with heparin.

Other anticoagulants are also used such as prostacyclin, sodium citrate, nafamostat mesylate, heparin-free haemodialysis etc. These methods, however, are either technically much more sophisticated, e.g. the one with citrate which is not appropriate for chronic use either, or quite expensive and thus their use is limited only to patients with the risk of bleeding, for whom heparin is not suitable.

On the other hand the extent of activation also depends upon the dialyser membranes used. Now two main groups of membranes are used i.e. biocompatible (synthetic) membranes and bioincompatible (cellulose) membranes. Cellulose membranes which are much cheaper, are used in more than 80% dialysis patients, but for the said membranes complement activation is characteristic which is most pronounced in the 15th minute of haemodialysis. The complement activation is essentially smaller when synthetic membranes are used. The complement activation has adverse effects in haemodialysis of the patients having acute and chronic renal failure, but because of rather high costs less than 20% of dialysis patients are dialysed using synthetic membranes which do not activate a complement.

An ideal solution would be the use of wholly inert membranes which however do not exist so far.

SUMMARY OF INVENTION

The object of the invention is a process for preventing the activation of enzyme systems in extracorporeal blood circulation in haemodialysis and in similar procedures such as coagulation and activation of complement system or bradykinin system, by means of sequential coagulation, wherein in the first 15 to 30 minutes of haemodialysis or of a similar procedure, sodium citrate or nafamostat mesylate, preferaly sodium citrate, is given into the dialysis line as the anticoagulant, then the adding of the heparin-free anticoagulant is stopped and there is started with the addition of heparin in a conventional total dose, this addition being carried out till the end of the dialysis.

The inventive process is universal for routine work.

BEST AND VARIOUS MODES FOR CARRYING OUT THE INVENTION

Figure 1:
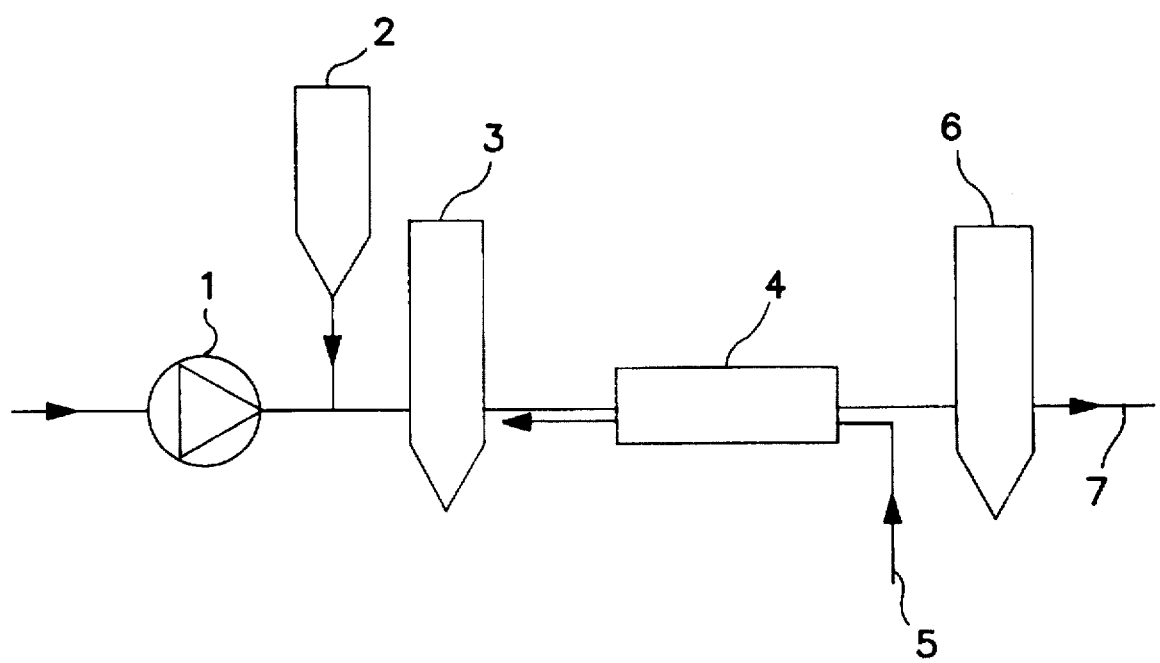
FIG. 1 illustrates a haemodialysis scheme wherein numeral 1 represents the blood pump, 2 the anticoagulant, 3 and arterial bubble trap, 4 a dialyser, 5 the flow of dialysis solution, 6 a venous bubble trap and 7 the blood stream.

The process is especially suitable when cellulose membranes are used since the complement activation is prevented thereby, and also when synthetic membranes are used since bradykinin activation (in addition to the prevention of the coagulation activation) is prevented.

Sodium citrate and nafamostat mesylate are well-known anticoagulants useful in dialysis. The same amounts of these agents per time unit are used as it is conventional heparin-free dialysis.

For the practical embodiment of sequential anticoagulation several variants may be arranged by medical staff with regard to given circumstances. It is however essential that novel characteristics of the inventive process as claimed be considered.

Sodium citrate, which binds calcium and magnesium ions, prevents the activation of coagulation and as well as the complement system. Thus the starting very pronounce complement activation at the use of the cellulose membrane, is prevented. After 15 to 30 minutes the dialysis membrane is not the same as in the beginning since it becomes more biocompatible due to of plasma proteins sticking thereto. Therefore the addition of heparin-free anticoagulant is no more necessary and the procedure may be continued with the conventional heparinization in a total or a minimum dose depending on the patient. The citrate is wholly eliminated by the end of dialysis as it is a small molecule which is dialysed well and nafamostat mesylate is not problematic either.

The process according to the invention may also be used also when using the AN69 membrane (polyacrylonitrile membrane) for the prevention of bradykinin activation and, consequently, of serious anaphylactic reactions and when using the LDL apheresis—Kaneka system, which is a procedure similar to haemodialysis, for eliminating LDL cholesterin (dextrane-sulfate column), whereby also the activation of bradykinin is prevented.

The invention is illustrated by the following non-limiting Example.

EXAMPLE

At the beginning of haemodialysis 4% sodium citrate was infused into the arterial line in the dosage of about 8% blood flow. The blood flow was small in the first 15 minutes of dialysis, 50 to 100 ml/min, and thus also the absolute dosage of citrate was small. During this time the dialysis solution was excluded from the circulation through the dialyser in order to prevent calcium supply and the need for elevating the citrate dosage. At the said citrate dosage, calcium did not need to be replaced. After 10 minutes of haemodialysis the starting dosage of conventional heparin was administered. After 15 minutes of haemodialysis the citrate infusion was stopped and it was started with the normal blood flow and dialysis solution flow (blood flow about 300 ml/min and dialysis solution flow 500 ml/min). Haemodialysis was carried out till the end in a conventional way.

It was proceeded in the same way at LDL apheresis.

I claim:

1. A process for preventing the activation of coagulation and activation of complement or bradykinin system during extracorporeal blood circulation which comprises:

adding citrate or nafamostat mesylate, in a concentration sufficient to prevent blood clotting, into the blood circulation line at the beginning of the extracorporeal blood circulation process;

stopping the addition of citrate or nafamostat mesylate after 15-30 minutes of the extracorporeal blood circulation process; and adding heparin, in a concentration sufficient to prevent blood clotting, into the blood circulation line until the end of the extracorporeal blood circulation process.

2. The process of claim 1 which comprises adding sodium citrate into the blood circulation line during the first 15 to 30 minutes of the extracorporeal blood circulation process.

3. The process of claim 1 in which the blood contacts a cellulose membrane during the extracorporeal blood circulation process.

4. The process of claim 1 in which the blood contacts a biocompatible synthetic membrane during the extracorporeal blood circulation process.

5. The process of claim 1 in which the blood contacts a polyacrylonitrile membrane during the extracorporeal blood circulation process.

6. The process of claim 1 wherein the extracorporeal blood circulation process is a low density lipoprotein cholestersol apheresis process.

7. The process of claim 1 wherein the extracorporeal blood circulation process is haemodialysis.

8. The process of claim 1 wherein adding said heparin begins when stopping the addition of said citrate or nafamostat.

* * * * *